(12) United States Patent
Hoffman et al.

(10) Patent No.: US 9,193,954 B2
(45) Date of Patent: Nov. 24, 2015

(54) METHODS AND COMPOSITIONS FOR MESENCHYMAL STEM CELL PROLIFERATION

(75) Inventors: Michael Hoffman, Rochester, NY (US); Danielle Benoit, Rochester, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 14/004,776

(22) PCT Filed: Apr. 2, 2012

(86) PCT No.: PCT/US2012/031806
§ 371 (c)(1),
(2), (4) Date: May 7, 2014

(87) PCT Pub. No.: WO2012/135813
PCT Pub. Date: Oct. 4, 2012

(65) Prior Publication Data
US 2014/0234960 A1 Aug. 21, 2014

Related U.S. Application Data

(60) Provisional application No. 61/470,315, filed on Mar. 31, 2011.

(51) Int. Cl.
*C12N 5/071* (2010.01)
*C12N 5/00* (2006.01)
*C12N 5/0775* (2010.01)

(52) U.S. Cl.
CPC ............ *C12N 5/0662* (2013.01); *C12N 5/0012* (2013.01); *C12N 5/0663* (2013.01); *C12N 2501/727* (2013.01)

(58) Field of Classification Search
None
See application file for complete search history.

(56) References Cited

U.S. PATENT DOCUMENTS

| | | |
|---|---|---|
| 2005/0265980 A1 | 12/2005 | Chen et al. |
| 2008/0194021 A1 | 8/2008 | Mays et al. |
| 2009/0111177 A1 | 4/2009 | Brivanlou et al. |
| 2010/0247494 A1* | 9/2010 | Gregory et al. .............. 424/93.7 |
| 2012/0100114 A1* | 4/2012 | Gregory et al. .............. 424/93.7 |
| 2012/0129178 A1* | 5/2012 | Lenz et al. .................. 435/6.12 |

OTHER PUBLICATIONS

De Boer et al (Tiss. Eng., 10(3/4):393-401 (2004).*
Boland et al., J. Cell. Biochem., 93:1210-1230 (2004).*
Chen et al., PNAS, 103(46):17266-17271 (2006).*
Sato, et al., Maintenance of pluripotency in human and mouse embryonic stem cells through activation of Wnt signaling by a pharmacological GSK-3-specific inhibitor, Nature Medicine, Dec. 21, 2003, vol. 10, No. 1, pp. 55-63.

* cited by examiner

*Primary Examiner* — Blaine Lankford
*Assistant Examiner* — Thomas J Visone
(74) *Attorney, Agent, or Firm* — Hodgson Russ LLP

(57) ABSTRACT

Provided is a method for increasing proliferation of mesenchymal stem cells. The method entails contacting the cells with 6-bromoindirubin-3'-oxime (BIO). This results in robust proliferation and "stemness" in a dose-dependent fashion, as indicated by the gene expression of two stem cell genes: Sox2 and Nanog.

8 Claims, 8 Drawing Sheets

METHODS AND COMPOSITIONS FOR MESENCHYMAL STEM CELL PROLIFERATION

CROSS REFERENCE TO RELATED APPLICATIONS

This application claims the priority of U.S. Provisional application No. 61/470,315, filed on Mar. 31, 2011, the disclosure of which is incorporated herein by reference.

BACKGROUND OF THE INVENTION

Bone marrow derived mesenchymal stem cells (MSCs) have been shown capable of differentiating down several tissue lineages, including bone, cartilage, fat, and tendon. For this reason these cells have been demonstrated as effective contributors in tissue-engineered applications for regenerative therapeutics, particularly in the areas of musculoskeletal repair. Using marrow aspirate MSCs can be easily isolated from a patient, expanded ex vivo, and reintroduced for therapeutic purposes. The use of MSCs in such tissue-engineering strategies relies heavily on both successful MSC proliferation as well as maintaining the ability for these proliferative cells to differentiate down mesenchymal lineages. Moreover, inducing controllable MSC proliferation in vivo proves advantageous in mimicking native healing cascades while ensuring the presence of an ample cell population to effectively contribute to injury remodeling. Such strategies enable tissue-engineering therapeutics to be achieved in regenerative medicine applications.

Currently MSCs can be expanded in vitro, using serum supplements (fetal bovine serum, autologous serum, platelet lysate, feeder-cells) but these approaches are transient in nature, require continual application in vitro, and often yield a highly heterogeneous MSC population. Furthermore, during extended culture, required to attain a therapeutically relevant cell number due to limited MSC numbers in bone marrow, cells exhibit an increasingly senescent phenotype, reduced proliferation, impaired homing capacity, and diminished differentiation potential. Reduced proliferative capacity in particular equates to a diminished long-term regenerative potential once these cells are transplanted for therapeutic purposes.

SUMMARY OF THE INVENTION

This invention provides a method for inducing proliferation in mesenchymal stem cells including human mesenchymal stem cells. In the present invention, we treated mesenchymal progenitor populations (human mesenchymal stem cells, hMSCs) in vitro with the soluble small molecule GSK3β inhibitor, 6-bromoindirubin-3'-oxime (BIO). Treatment induces robust proliferation and "stemness" in a dose-dependent fashion, as indicated by the gene expression of two stem cell genes: Sox2 and Nanog, to induce robust expansion of in vivo transplanted patient-specific stem cells and to provide homogeneous, multipotent cells for subsequent differentiation and tissue evolution to promote the healing of critical-sized defects.

In one aspect, the invention provides a method for inducing proliferation of mesenchymal stem cells comprising contacting the cells with a composition comprising 6-bromoindirubin-3'-oxime (BIO) in an amount sufficient to stimulate proliferation, which proliferation is greater than proliferation in the absence of BIO.

In another aspect, the invention provides a population of cells produced by the method of the present invention.

DETAILED DESCRIPTION OF THE INVENTION

Figure 1:
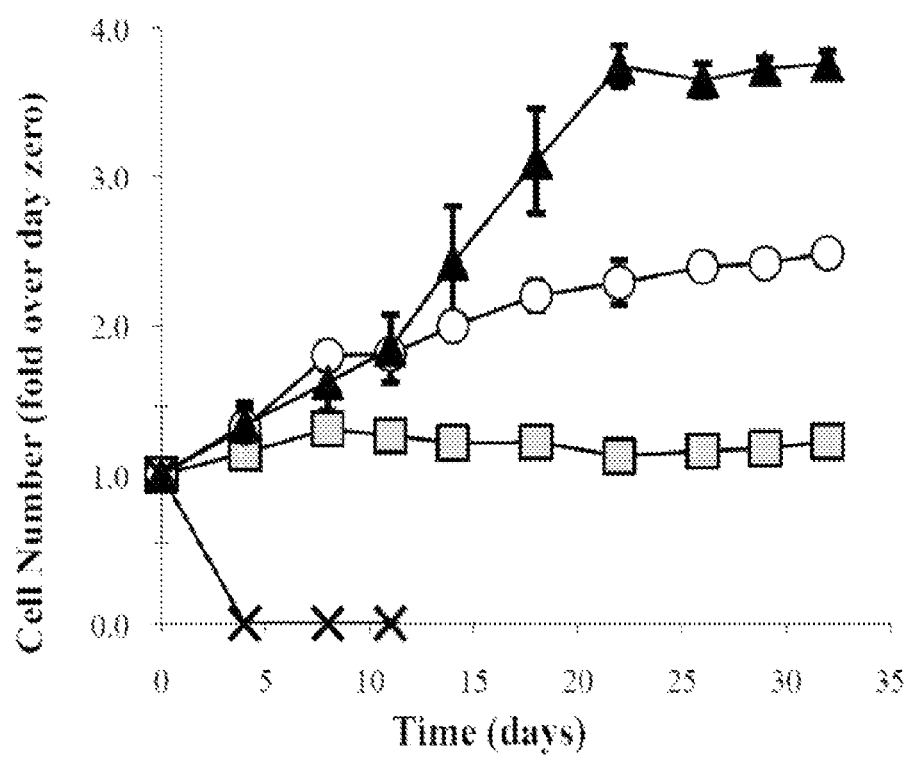
FIG. 1. Proliferative effect of BIO after 24 hr dosing; 0 µM (-□-, grey squares), 2 µM (-○-, open circles), 5 µM (-▲-, black triangles), 10 µM (-X-, black crosses). Proliferation was assessed using alamarBlue metabolic assay. Error bars shown are standard error (n=3).

The present invention provides the first evidence that the small molecule, glycogen synthase kinase 3 beta (GSK3β) specific inhibitor, 6-bromoindirubin-3'-oxime (BIO), acts to increase mesenchymal stem cell (MSC) proliferation. BIO-treated hMSCs retained their ability to differentiate down the traditional osteogenic, chondrogenic, adipogenic mesenchymal lineages. Gene analysis for the markers of osteogenic and adipogenic differentiation, Cbfa 1 and PPARγ indicated enhanced differentiation potential in BIO-treated cultures as compared to untreated controls. In addition to a ~4 fold population increase, gene expression also indicated an increased state of hMSC "stemness" based upon elevated Sox2 and Nanog expression. While not intending to be bound by any particular theory, it is considered that up regulation of Sox2, Nanog, and Oct4 contributes to a more homogeneous, pluripotent, and therefore proliferative hMSC population. Using a TOPFlash reporter plasmid we also demonstrate that BIO acts to increase concentrations of nuclear active β-catenin in a dose-dependent manner. While not intending to be bound by any particular theory, increases in β-catenin may enhance Wnt/β-catenin signaling, resulting in elevated transcription of downstream stem cell associated target genes (Sox2, Nanog, and Oct4) and increased MSC proliferation, in both two-dimensional culture conditions and encapsulated hydrogel networks. The results in the present invention make BIOs application in stem cell based transplantation therapeutics and regenerative medicine a viable opportunity.

The present invention provides a method of promoting the proliferation of mesenchymal stem cells. In one embodiment, the MSCs are human MSCs (hMSCs). The method comprises exposing MSC cells to inhibitor of glycogen synthase kinase 3β (GSK 3β). The cells can be exposed to the GSK 3β inhibitor in culture or after being administered/implanted/delivered into a subject. An example of such an inhibitor is 6-bromoindirubin-3'-oxime (BIO). In one embodiment, hMSC cells can be exposed in vitro and/or in vivo to BIO at a concentration sufficient to promote proliferation. In one embodiment, the cells are exposed to BIO for transient exposures (1 to 48 hours, for example 24 hours). In one embodiment, for exposing cells in culture, BIO is added so that the concentration in the cell culture media is from 0.1 to 10 µM (including all values therebetween to the tenth decimal place). In one embodiment, the final concentration can be 0.1, 0.5, 1.0, 1.5, 2.0, 2.5, 3.0, 3.5, 4.0, 4.5, 5.0, 5.5, 6.0, 6.5, 7.0, 7.5, and 8.0 µM. The cells can be exposed to BIO for various periods of time. In one embodiment, the cells are exposed for about 12-48 hours and then the culture medium containing BIO can be replaced with medium without BIO. Thus, in various embodiments, the cells can be exposed to BIO for not more than 12-48 hours, including all time points there between. For exposing cells that have been delivered to an individual; BIO can be delivered concomitantly with the cells or later or earlier (than the cells) in a localized or systemic manner. In one embodiment, it is delivered in a localized manner at or near the site of administered MSCs. For in vivo application, the cells are first treated with BIO vitro, allowed to proliferate and then can be implanted in vivo. After removal of BIO, the cells could be proliferated in culture. In one embodiment, the cells are proliferated for 3-30 days (and all integers therebetween). Proliferated cells could also be frozen for later use. In one embodiment, the number of cells is about 25 million cells. The number can vary depending upon the application and is determinable by those skilled in the art. In various embodiments, the invention accordingly provides a population of cells prepared by the method of the invention. The cells may cultured, or, isolated and/or purified to any desired degree of purification.

The cells can be proliferated on 2D substrates (such as culture dishes, multiwall clusters etc.) or can be proliferated using 3D scaffolds (such as polymeric gels, scaffolds etc.). For example, Poly(ethylene glycol) (PEG) can be used to form highly hydrated synthetic mesh networks whose physical properties (stiffness, elasticity, modulus) are comparable to native biological tissue, and whose chemical properties make it biologically inert. PEG macromers can be easily modified via chemical synthesis (degradable properties, tethered drug release, etc.), enabling precise control over the resultant mesh network.

In certain embodiments, the invention facilitates increased proliferation that is greater due to exposure to BIO than proliferation in the absence of BIO. Likewise, the invention facilitates greater expression of Sox2, Nanog, or combinations thereof, wherein the increased proliferation is greater due to exposure to BIO than proliferation in the absence of BIO.

In various embodiments, the invention provides for an increase of proliferation associated with exposure to BIO that is from 100% to 200% greater than proliferation in the absence of BIO. For example, we have demonstrated 2D proliferation of 155% and 172% (2 and 5 uM BIO, respectively) relative to that of untreated control, and 3D proliferation at 120% (5 uM BIO) relative to untreated control.

In various embodiments, the invention provides for an increase of expression of Sox2 and/or Nanog that is from 70% to 10,000%, including all integers there between, greater than an untreated control. For example, we have demonstrated increases of 677%, 797%, 545% (Sox2, Nanog, Oct4) relative to that of untreated controls on day 1 (2 uM BIO); increases of 9180%, 2247%, 1800% (Sox2, Nanog, Oct4) relative to that of untreated controls on day 1 (5 uM BIO); increase of 312%, 71%, 263% (Sox2, Nanog, Oct4) relative to that of untreated controls on day 3 (2 uM BIO); increases of 1238%, 324%, 755% (Sox2, Nanog, Oct4) relative to that of untreated controls on day 3 (5 uM BIO); and for 3D proliferation; increase of 220%-429%, 170%-232%, 249%-399% (Sox2, Nanog, Oct4) relative to that of untreated controls between days 1 and 18.

The structure of BIO is provided below:

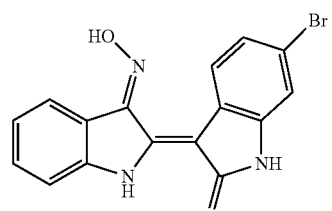

6-Bromoindirubin-3'-Oxime

The present invention can be used for increasing proliferation of MSCs. Such increased proliferation can be valuable in all the applications where MSCs are useful. For example, in addition to offering a means by which to enhance ex vivo expansion of MSCs, BIO may be utilized in combination with other tissue engineering approaches to therapeutically mimic native healing cascades in vivo. For example, periosteum precursor cells, similar in nature to MSCs surrounding the long bones of the body undergo robust proliferation in response to bone injury (i.e. fracture) initiating soft callus formation, subsequent mineralization, and eventual bone remodeling. Utilizing BIO-treated MSCs, in combination with a hydrated matrix environment robust proliferation could be achieved thereby augmenting periosteum function and aiding in bone repair, such as by introducing such compositions into an individual in need thereof.

The following Examples are meant to illustrate various embodiments of the invention but are not intended to be limiting.

EXAMPLE 1

A. BIO Induces hMSC Proliferation

The small molecule GSK3β inhibitor 6-bromoindirubin-3'-oxime was synthesized as previously described (Polychronopoulos et al., J Med Chem. 2004; 47(4):935-46). It is also commercially available (such as from Sigma). The molecule was solubilized in dimethyl sulfoxide (DMSO) to specified concentrations. hMSCs were plated at a density of 5,000 cell/cm2 in 24-well tissue culture plates. Cells were allowed to become adherent for a period of 24 hrs before BIO was introduced. 10 µL of BIO in DMSO were added to 1 mL of culture media so that the final concentrations of 2, 5, and 10 µM were achieved. The hMSCs were cultured with BIO-containing media for 24 hrs after which media was replaced by media without BIO. Culture continued over 33 days with media being replaced every three days. An alamarBlue cell viability assay was performed on days: −1 (before BIO treatment), 0, 4, 8, 12, 14, 17, 23, 26, 28, and 33. Cell population was normalized to alamarBlue readings after the initial period of 24 hr BIO dosing.

As illustrated in FIG. 1, BIO concentrations below 2 µM did not have a noticeable effect on hMSC population. BIO concentrations above 5 µM (10 µM) resulted in cell death. The range of 2-5 µM however resulted in a dose dependent proliferative response within the hMSC population. In a parallel study, it was determined that continual dosing with BIO results in complete cell death by day 5 (data not shown).

B. BIO Increases hMSC "Stemness"

Figure 2:
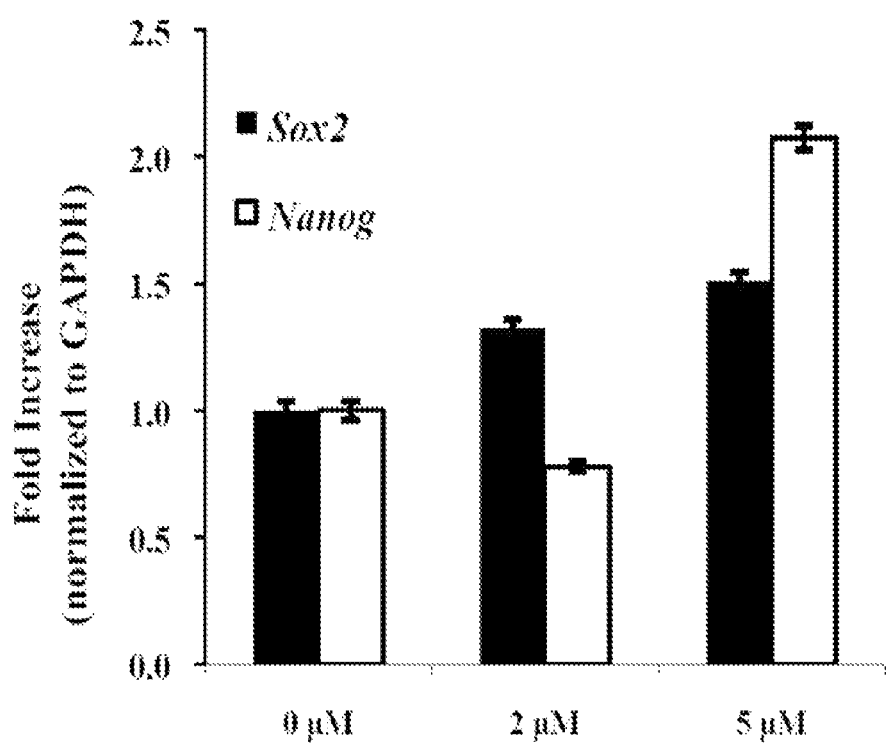
FIG. 2 RNA was harvested from BIO treated hMSCs at day 35 and analyzed for expression of stem markers Sox2 and Nanog. Expression was normalized to housekeeping gene GAPDH. Error bars shown are standard error (n=3).

At the end of the 33 day experimental time course RNA was isolated (Omega E.N.Z.A total RNA kit) from the hMSC specimens (n=3) and reverse transcription (Bio-Rad iSCRIPT cDNA synthesis kit) was performed to yield cDNA. Forward and reverse primers (Table 1.) for the stem markers Sox2 and Nanog as well as the housekeeping gene, GAPDH (Glyceraldehyde 3-phosphate dehydrogenase) were then used to quantify gene expression. Expressions of genes of interest (Sox2 and Nanog) were normalized to control (GAPDH) [4]. We observed a dose dependent increase in both Sox2 and Nanog gene expression. Sox2 expression increased ~30% and ~50% with 2 µM and 5 µM BIO treatment, while Nanog expression increased >100% with 5 µM BIO treatment (FIG. 2).

TABLE 1

Forward (FWD) and Reverse (REV) primer sequences

| Gene | Primer Sequence (5'-to-3') |
|---|---|
| Sox2 | FWD: AACCAGAAAAACAGCCCG (SEQ ID NO: 1) |
|  | REV: TTGCTGATCTCCGAGTTGTG (SEQ ID NO: 2) |
| Nanog | FWD: GATTTGTGGGCCTGAAGAAA (SEQ ID NO: 3) |
|  | REV: CAGATCCATGGAGGAAGGAA (SEQ ID NO: 4) |
| GAPDH | FWD: GCAAGAGCACAAGAGGAAGAG (SEQ ID NO: 5) |
|  | REV: AAGGGGTCTACATGGCAA (SEQ ID NO: 6) |

From this data we conclude that BIO dosing acts to increase hMSC proliferation by driving them towards a more stem-like state. While not intending to be bound by any particular theory, it be believed that as a GSK3β inhibitor, BIO acts to prevent the ubiquitination, and resultant degradation of β-catenin within the cytoplasm. Increased concentration of active β-catenin is then able to translocate into the nucleus where is binds to TCF/LEF (family of DNA binding transcription factors) and activates specific target genes that induce proliferation. From the data collected it appears that there are two distinct regimes to the proliferation curve; (1) an initial linear region of cellular proliferation, followed by a plateau phase. We consider that the initial linear proliferation is directly resultant from increased concentrations of active β-catenin within the cell. While this β-catenin remains active cellular proliferation is induced; once the levels of β-catenin returns to a normal range cellular proliferation stops.

EXAMPLE 2

2. Materials and Methods

All materials were purchased from Sigma-Aldrich unless otherwise specified.

2.1 Synthesis of 6-Bromoindirubin-3'-oxime (BIO)

The small molecule GSK3β inhibitor 6-bromoindirubin-3'-oxime (BIO) was synthesized as described in Example 1 (FIG. 2a). The resulting product was verified via NMR ($^1$H-NMR (DMSO, 400 MHz, δ ppm) 13.61 (1H, br s, NOH), 11.72 (1H, s, N'—H), 10.85 (1H, s, N—H), 8.53 (1H, d, H-4), 8.19 (1H, d, H-4'), 7.39 (2H, br s, H-6', 7'), 7.07 (1H, d, H-5), 7.01 (2H, br s, H-7, 5') and matrix-assisted laser desorption/ionization time of flight (MALDI-TOF) mass spectroscopy (m/z 356 g/mol).

2.2 Synthesis of Poly(Ethylene Glycol) (PEG) Macromers Poly(Ethylene Glycol) Dimethacrylate (PEGDM)

Methacrylation of linear PEG (Alfa Aesar) with average molecular weight 10 kDa was performed. Methacrylic anhydride was combined with PEG at a molar ratio of 5:1 (methacrylic anhydride:PEG) in a glass scintillation vial. The vial was then microwaved (1100 W, Sharp conventional household microwave) for 5 min in the hood stopping every 30-60 seconds to vortex the reaction. The reaction was cooled to room temperature and the product was dissolved in dichloromethane, and precipitated three times in cold ethyl ether, collected by filtration, and dried under vacuum. Dialysis was performed against deionized water using a membrane with a molecular weight cutoff of 3500 Da (Spectrum Labs, Rancho Dominguez, Calif.). Numerous water exchanges were made over a period of 24 hrs and the purified product was obtained through lyophilization (FreeZone 2.5, Labconco). PEGDM percent methacrylation was calculated using $^1$H-NMR analysis by comparing the area under the peaks from methacrylate functional groups (δ=5.6, 1H/end and 6.1, 1H/end) with the peak from the PEG backbone (δ=3.64, 908H). Macromers had greater than 95% dimethacrylate functionalization.

Synthesis of Acrylate-PEG-RGDS

The amino acid sequence Arg-Gly-Asp-Ser (RGDS; 433 g/mol) (EMD Chemicals, San Diego, Calif.) was coupled to acrylated-PEG through the amino terminus by dissolving 20 mg of peptide in 2 mL of dimethyl sulfoxide (DMSO) and adding a single drop of N,N-Diisopropylethylamine (DIEA). To this, acrylate-PEG-N-Hydroxysuccinimide (acrylate-PEG-NHS, MW 3500, Jenkem Technology, Beijing China, m/z 3707 g/mol) was added at a molar ratio of 1:1.1 (peptide to acrylate-PEG-NHS). The reaction was vortexed for 1 min and then allowed to incubate overnight with gentle agitation. The product was dialyzed against deionized water (molecular weight cutoff=1000 Da, Spectrum Labs, Rancho Dominguez, Calif.) over 24 hrs with multiple deionized water exchanges. The product was lyophilized and analyzed via matrix-assisted laser desorption/ionization time of flight (MALDI-TOF) mass spectroscopy to verify molecular weight (m/z Na+, 4070 g/mol), and stored at 4° C.

2.3 The Effect of BIO on Two-Dimensionally Treated Mesenchymal Stem Cell (hMSC) Functions Cell Culture Human mesenchymal stem cells (hMSCs) were isolated from human donor bone marrow obtained from Lonza (Walkersville, Md.) using conventional techniques. Briefly, bone marrow aspirate was plated at 10 μL/cm$^2$ with 10 mL low-glucose Dulbecco's Modified Eagle Medium (Thermo) supplemented with 10% Fetal Bovine Serum (FBS) (Atlanta Biologicals, Lawrenceville, Ga., USA), 100 units/ml penicillin (Lonza), 100 μg/ml streptomycin (Lonza), 0.25 μg/ml amphotericin B (Lonza), and 10 ng/mL basic fibroblast growth factor (bFGF) (BD Biosciences, Bedford, Mass.). Aspirate was incubated for 7 days untouched at 37° C. and 5% $CO_2$. After 7 days media was replaced and adherent hMSCs were split and passaged. It should be noted that bFGF was only used during initial hMSC culture expansion. bFGF was not used in media during BIO studies. In this study hMSCs at passage 3 were used for all studies.

Mouse embryonic fibroblasts (C3H10T1/2, Clone 8) were obtained from American Type Culture Collection (ATCC) (Manassas, Va.). C3H10T1/2s were grown at 37° C. and 5% $CO_2$ in Basal Medium Eagle (BME) (cellgro) supplemented with 10% Fetal Bovine Serum (FBS) (Atlanta Biologicals, Lawrenceville, Ga., USA), 100 units/ml penicillin (Lonza), 100 μg/ml streptomycin (Lonza), 0.25 μg/ml amphotericin B (Lonza) (BME media).

Figure 4:
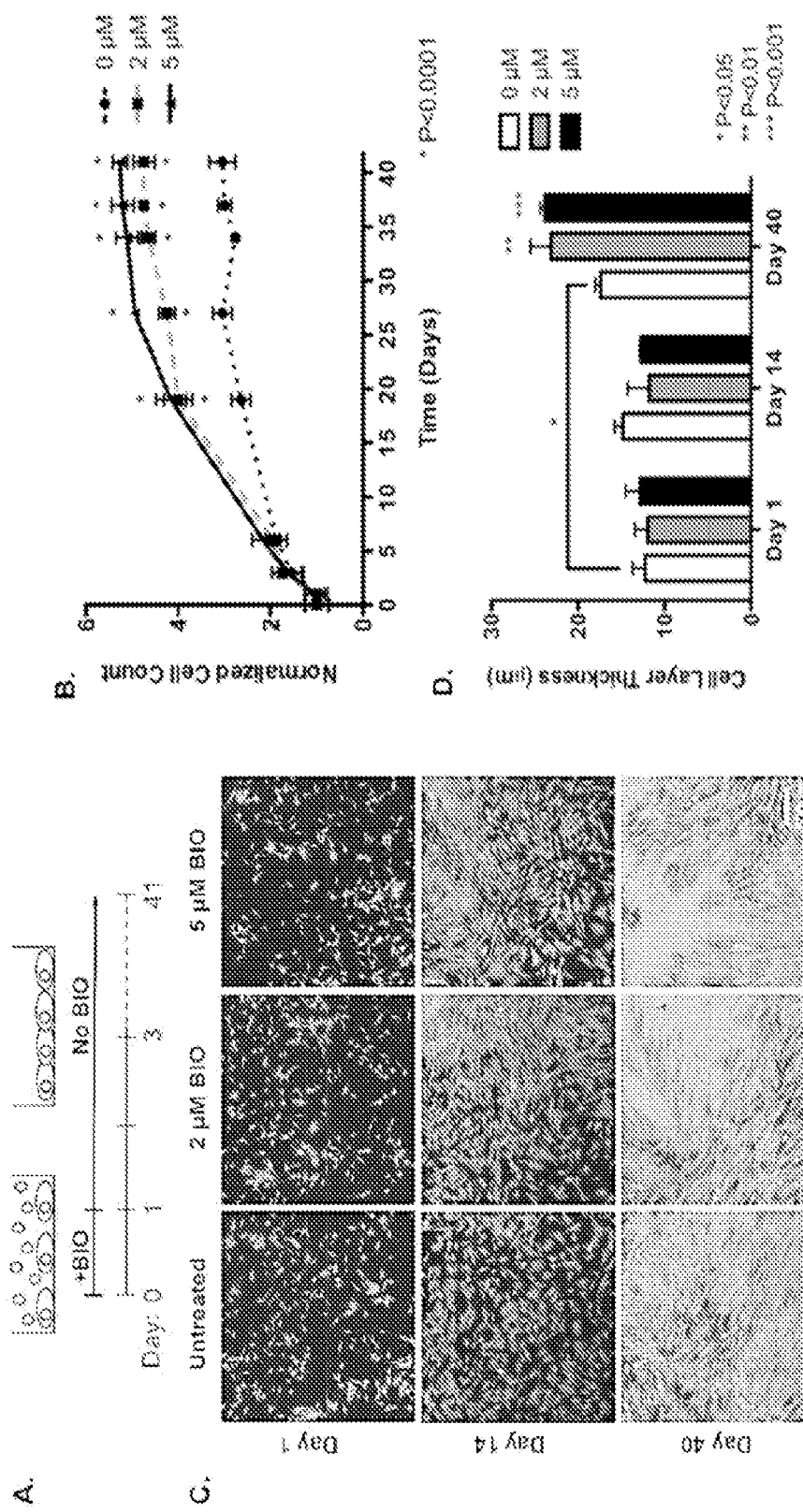
FIG. 4 Schematic representation of 41 day hMSC monolayer culture after 24 hr exposure to BIO-containing media (A). Cells were trypsinized and manually counted on days 0, 1, 3, 6, 19, 27, 34, 37, and 41 and shown to undergo a dose-dependent, BIO-mediated increase in proliferation (B). LIVE/DEAD confocal imaging of two-dimensional BIO-treated hMSC cultures revealed increased cell stacking compared to untreated controls (C), and an associated increase in cell layer thickness (D). Images revealed nearly 100% live cells with no detectable dead cells.
Figure 7:
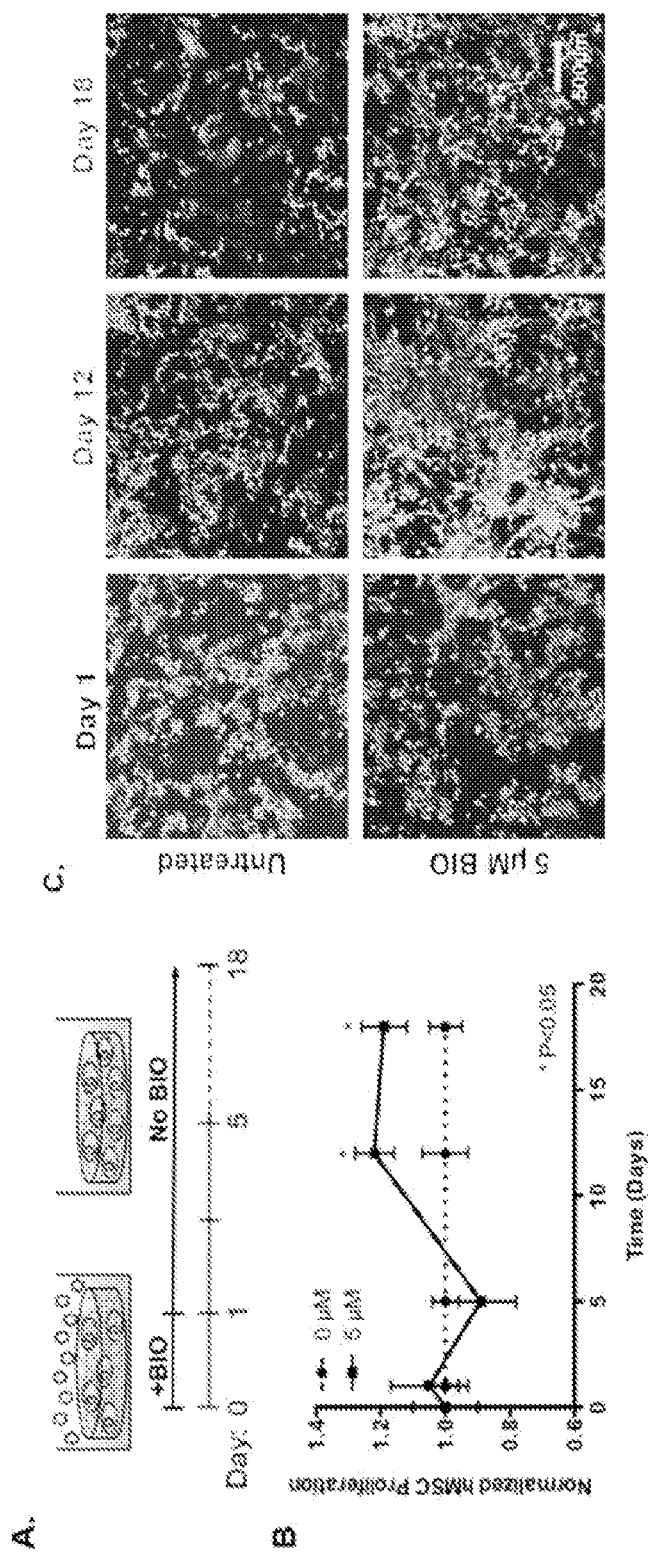
FIG. 7 Schematic representation of 18 day PEG-encapsulated hMSC culture after 24 hr exposure to BIO-containing media (A). Cell DNA concentration was quantified on days 0, 1, 5, 12, and 18 and shown to undergo a dose-dependent, BIO-mediated increase in proliferation (B), as previously shown in two-dimensional cultures. Representative LIVE/DEAD confocal images of PEG-encapsulated BIO-treated hMSC cultures (C). Images revealed nearly 100% live cells with no detectable dead cells.

Cell Treatment with BIO hMSCs or C3H10T1/2s were seeded at a density of 5,000 cell/cm$^2$ in 24-well tissue culture plates (Greiner Bio-One, Monroe, N.C.) and allowed to become adherent over a period of 24 hrs prior to treatment. BIO was solubilized in dimethyl sulfoxide (DMSO) to prepare 200 and 500 μM stock solutions. 10 μL of BIO in DMSO was added to 1 mL of culture media so that the final concentrations of 0, 2, and 5 μM were achieved. The cells were cultured with BIO-containing media for 24 hrs after which media was replaced by media without BIO, as illustrated in FIGS. 4a and 7a (two-dimensional treatment and three-dimensional treatment respectively).

Analyzing β-Catenin Activity in C3H10T1/2s after BIO Treatment

The β-catenin TOPFlash reporter plasmid and the FOPFlash mutant control (Addgene Plasmid #12456, and Addgene Plasmid #12457 were obtained in the form of DH5alpha bacterial stabs. Bacteria were streaked onto ampicillin-containing agar plates and grown overnight at 37° C. A single colony was selected, grown in 50 ml Luria-Bertani (LB) broth with 100 μg/ml ampicillin (Gibco) to select for ampicillin resistant colonies, and cultured at 37° C. under constant agitation for 24 hrs. Bacteria were centrifuged to form a pellet and plasmid DNA was purified using a Plasmid Midi Kit (Qiagen). Plasmid DNA was digested using EcoRI and PvuI restriction endonucleases (New England Biolabs) and fragments were separated on a 0.8% agarose gel. Molecular weights were verified using a standard DNA ladder (HyperLadder I, BioLine).

Figure 3:
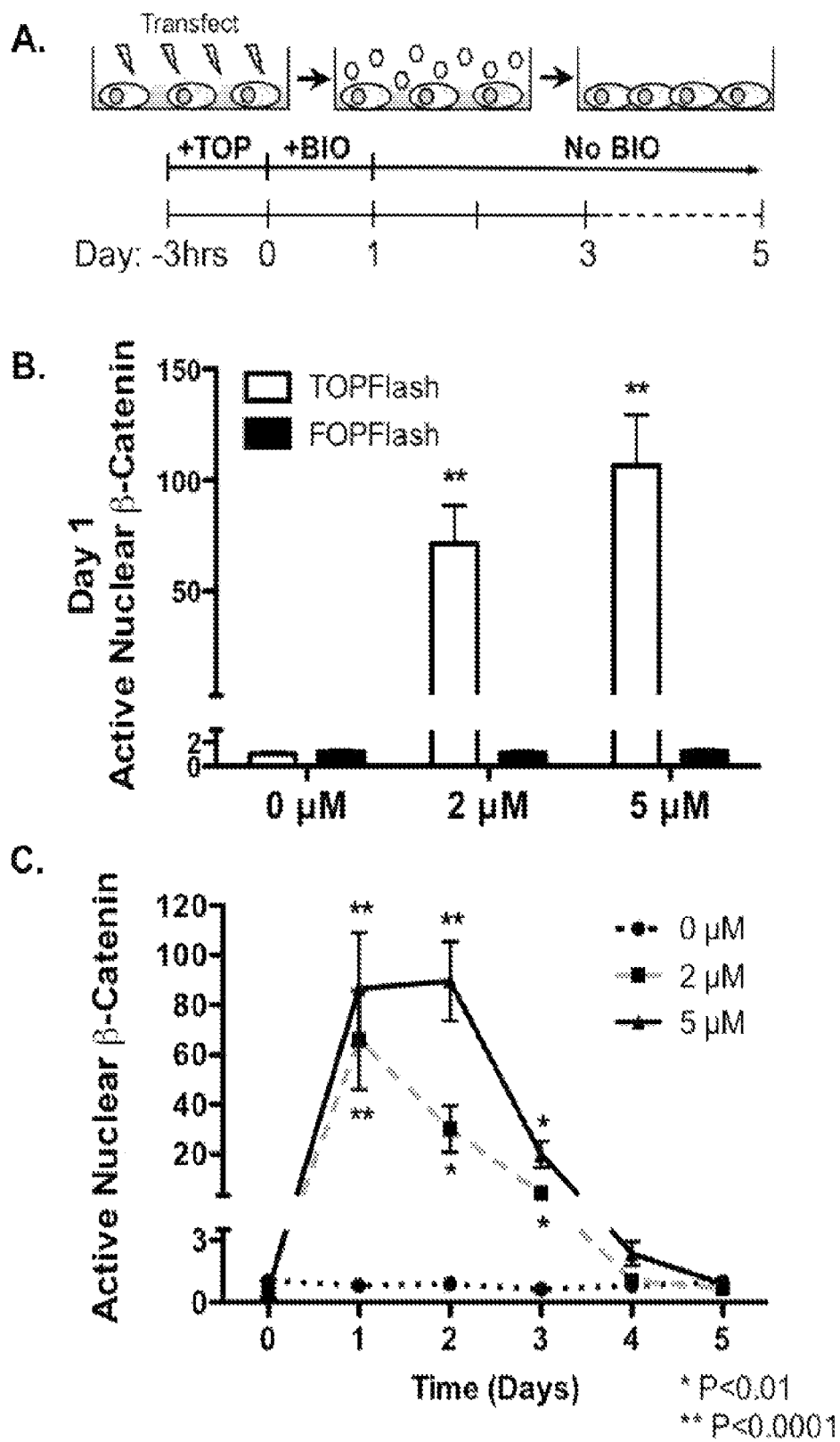
FIG. 3 Schematic representation of 3 hr C3H10T1/2 transfection with TOP/FOPFlash DNA plasmid followed by 24 hr exposure to BIO-containing media and subsequent analysis for active nuclear β-catenin over 5 days (A). Active nuclear β-catenin concentrations (TOPFlash) show a BIO-mediated dose-dependent increase immediately after BIO treatment as compared to control plasmid (FOPFlash) (B). Increased active nuclear β-catenin concentrations persists for 3 days after BIO-treatment before returning to basal levels (C).

C3H10T1/2 mouse embryonic fibroblasts were seeded in multiple 48-well plates and treated with BIO containing growth media for 24 hrs to analyze the effects of β-catenin activity over time. Cells were transfected with plasmid DNA using Lipofectamine LTX and PLUS reagents (Invitrogen) (FIG. 3a). Two master solutions were created and allowed to incubate individually for 15 min at room temperature; 0.4 μg plasmid DNA, 4 μl PLUS, and 25 μl Opti-MEM (Gibco) (per well), and 2.8 μl Lipofectamine LTX and 25 μl Opti-MEM (per well). The two solutions were combined and allowed to incubate for an additional 15 min. Cells were washed with PBS and then 50 μl of DNA-Lipofectamine-Opti-MEM solution was added to each well with 150 μl of high-glucose Dulbecco's Modified Eagle Medium (Thermo) containing no FBS, penicillin, streptomycin, or amphotericin B. Cells were incubated at 37° C. and 5% $CO_2$ for 3 hrs. The transfection media was then removed and replaced with medium containing 0, 2, or 5 μM BIO. Cells were incubated at 37° C. and 5% $CO_2$ for 24 hrs, after which BIO containing media was removed and replaced with normal BME media.

Luciferase activity was measured prior to BIO treatment (day 0), as well as on days 1, 2, 3, 4, and 5 after the 24 hr BIO treatment period. Media was aspirated from C3H10T1/2s and the cells were washed with PBS. To each well 150 μl of 1× Luciferase Cell Culture Lysis Reagent (Promega, Madison, Wis.) was added and allowed to incubate at room temperature for 20 min before sonication to ensure total cell lysis (Fisher Scientific, Sonic Dismembrator Model 100). 20 μl of sample lysate was transferred to a white 96-well plate in triplicate. To each 96-well 25 μl of Luciferase Assay Reagent (Promega, Madison, Wis.) was added and total luminescence was measure immediately using a BioTek Synergy Mx plate-reader. Total luminescence was normalized to cellular DNA concentration using a Quant-iT PicoGreen dsDNA Assay Kit (Invitrogen) to account for well-to-well variability in cell density.

Analyzing the Effects of BIO on hMSC Proliferation

During culture, hMSC viability was periodically assessed using an alamarBlue metabolic assay (AbD Serotec, UK). Culture media was replaced with a 10% alamarBlue-media solution and allowed to incubate at 37° C. for 2 hr. After incubation, alamarBlue solution was transferred to black 96-well plates and media was refreshed. Fluorescence intensity was measured using a Tecan Infinite 200 PRO plate-reader (excitation/emission: 570/600 nm). To assess hMSC proliferation, cells were trypsinized and counted using trypan blue exclusion and a hemocytometer. Average cell counts were normalized to data collected on day 0 to illustrate the effect of BIO on hMSC proliferation over time.

Assessment of hMSC Cell Layer Thickness hMSC cell layer thickness was measured using the z-directional controls of a FV1000 Olympus Laser Scanning Confocal Microscope. On days 1, 14, and 40 cells, seeded on optically clear glass bottom 24-well culture plates (MatTek, Ashland, Mass.) were stained using a fluorescent LIVE/DEAD Viability/Cytotoxicity kit (Invitrogen). The focal plane of the microscope was adjusted to the cell-plate interface and set to zero. Using the z-directional controls the focal plane was raised until the live fluorescently stained cells were no longer visible at which point the cell layer thickness was recorded.

Figure 6:
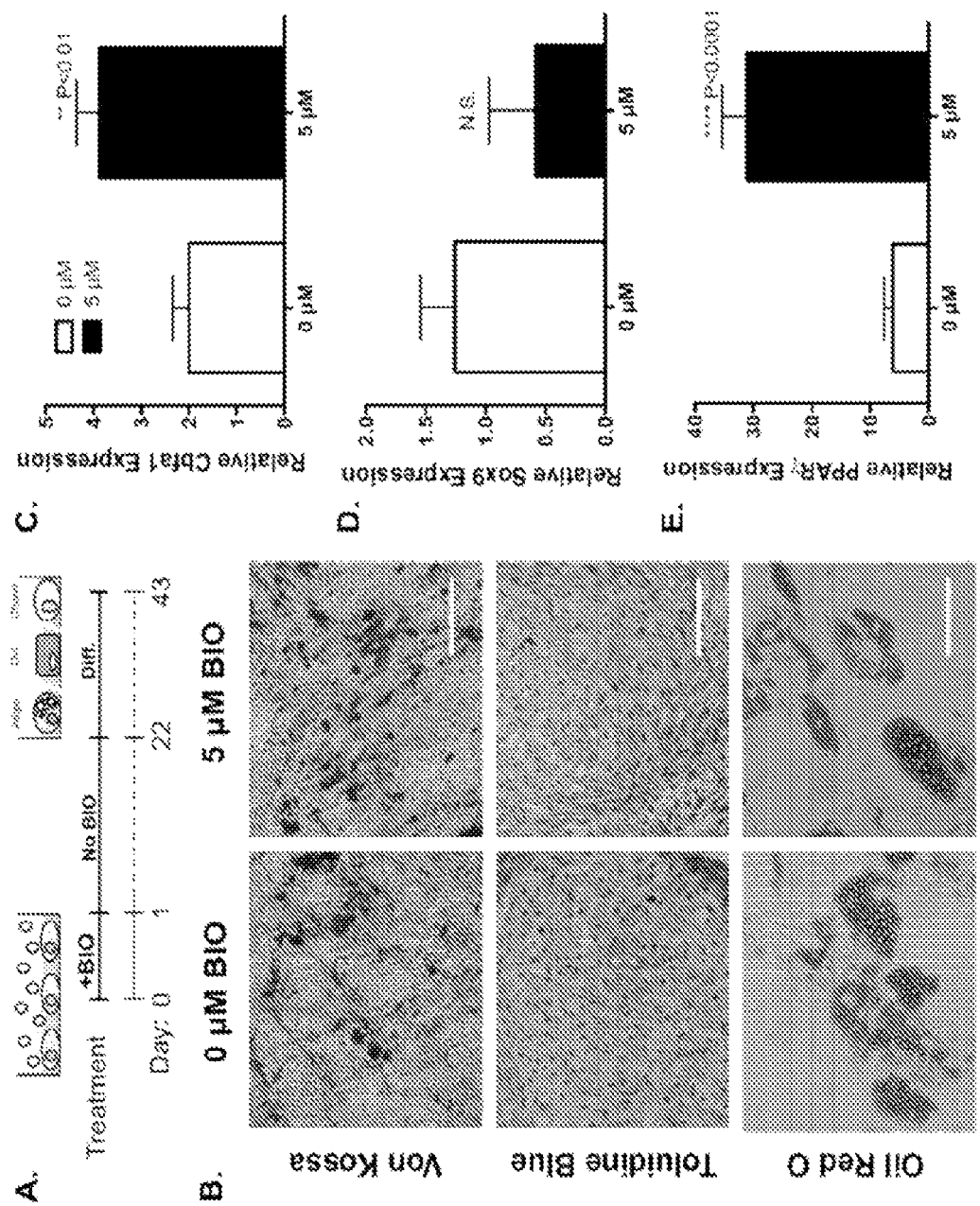
FIG. 6 Schematic representation of media induced differentiation of BIO-treated hMSCs (A). After 24 hr BIO treatment cells were allowed to proliferate for 3 weeks before being treated with supplements for an additional 3 weeks to induce osteogenesis (von Kossa), chondrogenesis (toluidine blue), and adipogenesis (oil red o) (B). Panels C, D and E provide graphical summarizes of relative gene expression profiles for Cbfa1, Soc9 and PPARγ, respectively.

Analyzing the Effects of BIO on hMSC Differentiation hMSCs treated with BIO, and allowed to proliferate for 21 days were differentiated into osteogenic, chondrogenic, and adipogenic lineages as previously described (See, for example, Jaiswal N, Haynesworth S E, Caplan A I, Bruder S P. Osteogenic differentiation of purified, culture-expanded human mesenchymal stem cells in vitro. J Cell Biochem. 1997; 64(2):295-312; Mackay A M, Beck S C, Murphy J M, Barry F P, Chichester C O, Pittenger M F. Chondrogenic differentiation of cultured human mesenchymal stem cells from marrow. Tissue Eng. 1998; 4(4):415-28; McBeath R, Pirone D M, Nelson C M, Bhadriraju K, Chen C S. Cell shape, cytoskeletal tension, and RhoA regulate stem cell lineage commitment. Dev Cell. 2004; 6(4):483-95.) Briefly, for osteogenic and adipogenic differentiation, hMSCs were seeded at a density of 5,000 cell/cm² in 24-well tissue culture plates, allowed to become adherent, and treated with BIO containing growth media (0 or 5 µM) for 24 hrs. After 24 hrs cell media was replaced and cells were allowed to proliferate over three weeks. After three weeks BIO-treated hMSCs were cultured for three weeks in standard differentiation-inducing media (FIG. 6a). For osteogenic differentiation hMSCs were grown in normal growth media with osteogenic supplements (100 nM dexamethasone, 10 mM β-glycerophosphate, 50 µM ascorbic acid-2-phosphate). Similarly, for adipogenic differentiation, hMSCs were cultured with adipogenic supplements, switching between 3 days in adipogenic differentiation medium (1 µM dexamethasone, 0.2 mM indomethacin, 10 µg/mL insulin, 0.5 mM methylisobutylxanthine) and 1 day in adipogenic maintenance medium (10 µg/mL insulin) McBeath et al., (2004). Differentiated two-dimensional cell cultures were fixed in 24-well tissue culture plates for 48 hrs in 4% paraformaldehyde and the monolayers were stained for mineralization (von Kossa, osteogenic), or the presence of lipid droplets (oil red o, adipogenic). Undifferentiated cultures were also stained as negative controls. Images were taken on a Motic AE20 inverted light microscope using a Canon EOS Rebel T2i with an eyepiece modification.

For chondrogenic differentiation, hMSCs were seeded at a density of 5,000 cell/cm² in T-75 tissue culture flasks, allowed to become adherent, and treated with BIO containing growth media for 24 hrs. After 24 hrs, cell media was replaced and cells were allowed to proliferate over three weeks (FIG. 6a). After three weeks, BIO-treated hMSCs were placed into pellet cultures (250,000 cells/pellet) and cultured with chondrogenic supplements (10 ng/mL TGF-$\beta_3$, 100 nM dexamethasone, 50 µg/mL ascorbic acid-2-phosphate, 100 µg/mL sodium pyruvate, 40 µg/mL proline, and ITS-plus) (Mackay et al., 1998). Pellet cultures were fixed for 48 hrs in 4% paraformaldehyde, cryosectioned, and stained for glycosaminoglycan production (toluidine blue, chondrogenic). Stained sections were imaged as described above.

Evaluation of BIO-Mediated Alterations in hMSC Gene Expression

RT-PCR was used to assess gene expression of hMSCs over time. At days: 0 (before BIO treatment), 1, 3, 6, 19, 29, 34, 37, and 41, samples were lysed and total RNA was isolated (ENZA Total RNA Kit, Omega). Reverse transcription was performed using the iScript cDNA Synthesis Kit (Bio-Rad). The reverse transcription reaction was incubated at 25° C. for 5 min, 42° C. for 30 min, and terminated at 85° C. for 5 min. PCR was performed using a CFX96 Real-Time PCR System (Bio-Rad), monitoring sybrgreen products (SsoFastEvaGreen Master Mix, Bio-Rad). Primers for β-actin, sex determining region Y-box 2 (Sox2), Nanog homobox (Nanog), and octamer-binding transcription factor 4 (Oct4), core-binding factor subunit alpha-1 (Cbfa1, also known as Runx2), sex determining region Y-box 9 (Sox9), and peroxisome proliferator-activated receptor gamma (PPARγ) were used (Table 2). The PCR parameters used were as follows: hold at 95° C. for 5 min, followed by 40 cycles of: 95° C. for 15 sec denaturation, 60° C. (β-actin, Sox2, Sox9), or 57° C. (Nanog, Oct4, Cbfa1), or 55° C. (PPARγ) for 60 sec annealing, and 72° C. for 20 sec extension. Threshold cycle (CT) analysis was used to quantify PCR products normalized to the cellular housekeeping gene β-actin. Relative gene quantification was performed using the Pfaffl Method, taking into account the variation between primer efficiencies.

TABLE 2

Forward (FWD) and Reverse (REV) Primer Sequences Utilized in this Work

| Gene | Primer Sequence (5'-to-3') | $R^2$ | Efficiency | Anneal. |
|---|---|---|---|---|
| B-actin | FWD: TGTGATGGTGGGAATGGGTCAG (SEQ ID NO: 7)<br>REV: TTTGATGTCACGCACGATTTCC (SEQ ID NO: 8) | 0.9900 | 82% | 60° C. |
| Sox2 | FWD: AACCAGAAAAACAGCCCG (SEQ ID NO: 1)<br>REV: TTGCTGATCTCCGAGTTGTG (SEQ ID NO: 2) | 0.9619 | 122% | 60° C. |
| Nanog | FWD: GATTTGTGGGCCTGAAGAAA (SEQ ID NO: 3)<br>REV: CAGATCCATGGAGGAAGGAA (SEQ ID NO: 4) | 0.9803 | 91% | 57° C. |
| Oct4 | FWD: CTGAAGCAGAAGAGGATCAC (SEQ ID NO: 9)<br>REV: GACCACATCCTTCTCGAGCC (SEQ ID NO: 10) | 0.9369 | 83% | 57° C. |
| Cbfa1 | FWD: ATGCTTCATTCGCCTCACAAAC (SEQ ID NO: 11)<br>REV: CCAAAAGAAGTTTTGCTGACATGG (SEQ ID NO: 12) | 0.9899 | 90% | 57° C. |
| Sox9 | FWD: TTTCCAAGACACAAACATGA (SEQ ID NO: 13)<br>REV: AAAGTCCAGTTTCTCGTTGA (SEQ ID NO: 14) | 0.9340 | 120% | 60° C. |

TABLE 2-continued

Forward (FWD) and Reverse (REV) Primer Sequences Utilized in this Work

| Gene | Primer Sequence (5'-to-3') | $R^2$ | Efficiency | Anneal. |
|---|---|---|---|---|
| PPARγ | FWD: TCTCTCCGTAATGGAAGACC (SEQ ID NO: 15)<br>REV: GCATTATGAGACATCCCCAC (SEQ ID NO: 16) | 0.9468 | 105% | 55° C. |

2.4 The Effect of BIO on PEG-Encapsulated hMSC Function
Photoencapsulation of hMSCs in PEG Hydrogels A 10 wt % solution of PEGDM was prepared in phosphate buffered saline (PBS) with 2.0 mM acryloyl-PEG-RGDS. The photoinitiator lithium phenyl-2,4,6-trimethylbenzoylphosphinate (LAP) was synthesized using conventional techniques and added at a final concentration of 0.05 wt %. Trypsinized hMSCs were centrifuged to form pellets and counted. The PEG macromer solution was added to the cell pellet, and volumes were adjusted to achieve a final cell concentration of 25 million cells/mL. Using a sterile 1 mL syringe with the tip removed as a mold, 40 µL of PEG/cell solution was added and exposed to long-wavelength 365 nm light (5 mW/cm$^2$ intensity) for 10 min at room temperature. After photopolymerization was complete, the cell/hydrogel disks were removed from the syringes and placed in 24-well tissue culture plates (Greiner Bio-One, Monroe, N.C.) with growth media. The constructs were cultured up to 3 weeks at 37° C. and 5% CO$_2$ with media changes occurring every three days.

Encapsulated hMSC viability, BIO treatment, and assessment of gene expression was performed as described in Section 2.3 with exception of cell lysate collection. For assessment of gene expression hMSC-PEG constructs were homogenized in lysis buffer and centrifuged to pellet polymerized PEG. The supernatant was then collected for analysis.

Encapsulated hMSC Proliferation Analysis

Encapsulated hMSC proliferation was assessed using total cellular DNA concentration, assuming constant DNA per cell, using a Quant-iT PicoGreen dsDNA Assay Kit (Invitrogen). Average encapsulated DNA concentrations were normalized to data collected on day 0 to illustrate BIOs effect on hMSC proliferation over time.

2.5 Statistical Analysis

All data is presented as mean±standard deviation unless otherwise noted. In all cases, at least three replicate samples were averaged for each data point. Statistics were assessed with GraphPad Prism Software using a two-way ANOVA with Bonferroni post-hoc analysis.

3. Results 3.1 BIO-Mediated Enhancement of Active Nuclear β-catenin

To verify BIO's efficacy as a GSK3β-specific inhibitor within the Wnt/β-catenin signaling pathway, active nuclear β-catenin concentrations were quantified using TOPFlash/FOPFlash reporter plasmids both before and after treatment with 0, 2, and 5 µM BIO containing media (FIG. 3a). Mouse embryonic fibroblasts (C3H10T1/2s) were used. Normalization of TOPFlash relative luminescence units (RLU) to associated cellular DNA concentrations yielded a BIO-mediated, dose-dependent, statistically significant increase in nuclear β-catenin activity after 24 hr treatment. As illustrated in FIG. 3b, C3H10T1/2 cultures exhibited a 106-fold increase in normalized TOPFlash signal compared to untreated controls after 24 hr treatment with 5 µM BIO. Similarly, the cultures treated with 2 µM BIO exhibited a 71-fold increase over untreated controls. Furthermore, enhanced β-catenin signaling, as observed through elevated TOPFlash signaling, persisted for an additional three days after BIO was removed from the culture media before returning to basal levels (FIG. 3c).

3.2 Proliferative Effect of BIO on Two-Dimensionally Treated hMSCs

To evaluate the effect of BIO on hMSC proliferation, cells were counted manually just before, and 1, 3, 6, 19, 27, 34, 37, and 41 days after treatment with BIO (0, 2, and 5 µM) for a 24 hr period (FIG. 4a). The results shown in FIG. 4b are normalized to the initial cell population obtained on day 0. Normalized cell populations increased in a dose-dependent fashion over the culture time. At day 41, hMSCs treated with 2 µM or 5 µM BIO containing media exhibited a 4.5- and a 5.5-fold increase in cell population, respectively, compared to untreated controls (0 µM BIO).

It should be noted that by day 18, all experimental groups (0, 2, and 5 µM) had reached confluence based on visual inspection. To further investigate how BIO was enhancing hMSC proliferation beyond the limits of observed two-dimensional contact inhibition, hMSC expansion was examined using LIVE/DEAD staining and confocal microscopy. Qualitative assessment of images taken on day 14 shows that BIO-treated cells are more confluent than the untreated controls (FIG. 4c). This trend continues in the day 40 images where there are noticeably denser regions of cell growth in both the 2 and 5 µM BIO-treated cultures, while the untreated controls look uniformly confluent. Closer analysis of the 2 and 5 µM BIO treated cultures at day 40 revealed distinctive cell-stacking, with sheet thicknesses reaching 2 to 3 cells thick (FIG. 4c). Using the z-directional controls of the confocal microscope cell layer thickness was further quantified. At day 40, hMSC cultures treated with 2 µM or 5 µM BIO containing media exhibited a significant increase in cell layer thickness, 23.5 µm and 24.0 µm respectively, as compared to the untreated control (17.5 µm), illustrated in FIG. 4d. Measurements made at day 0 and 14 respectively showed no statistically significant differences between groups. These confocal thickness measurements are consistent with our initial cell counts (FIG. 4b), leading to the conclusion that BIO-treatment is playing a role in enhancing hMSC proliferation.

3.3 BIO-Treated hMSC Gene Expression

Figure 5:
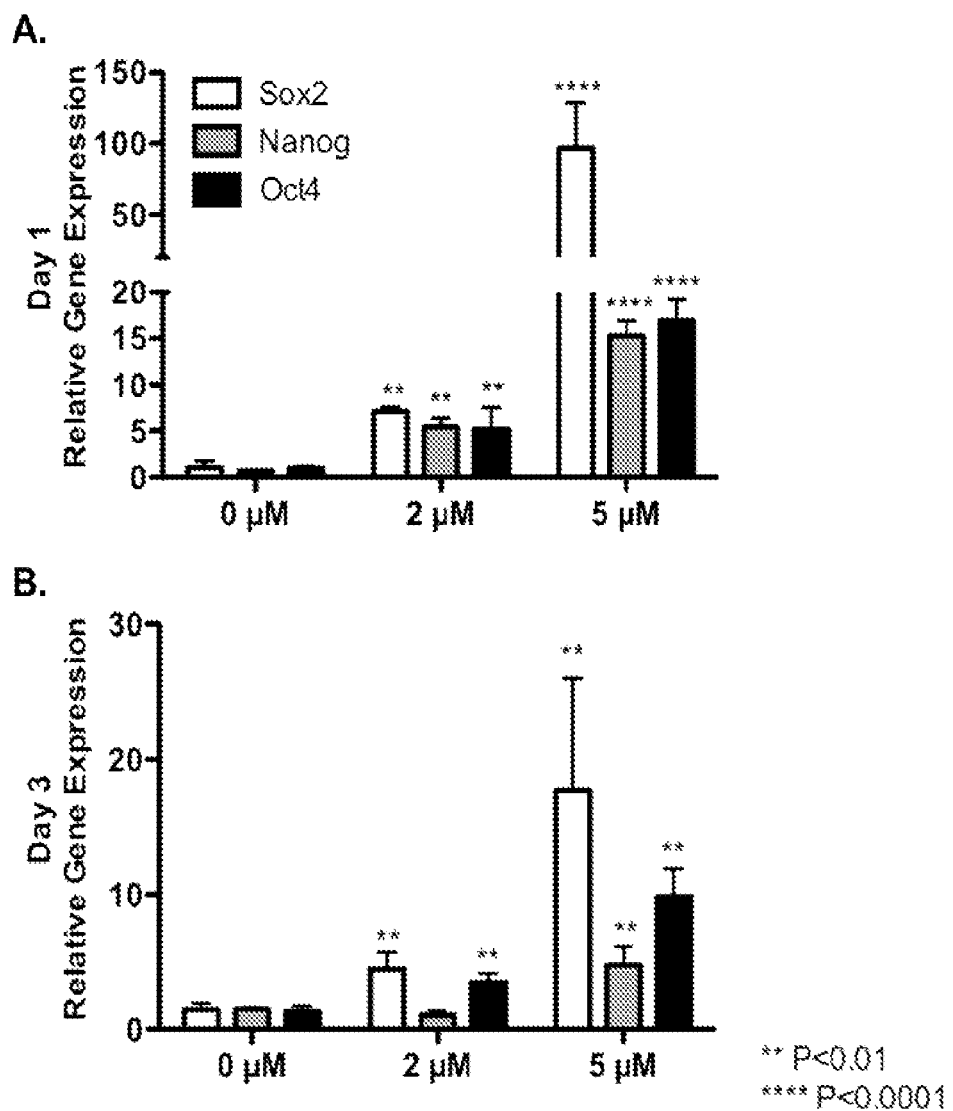
FIG. 5 Gene profiles showing elevated expression of the markers of undifferentiated stem cells, Sox2, Nanog, and Oct4 on day 1 (A), and day 3 (B) following 24 hr exposure of two-dimensionally cultured hMSCs to BIO-containing media.

To more closely examine BIO's effects on hMSCs gene expression profiles for the markers of undifferentiated stem cells sex determining region Y-box 2 (Sox2), Nanog homobox (Nanog), and octamer-binding transcription factor 4 (Oct4) were monitored and normalized to the housekeeping gene β-actin. This was done to both ensure that BIO treatment was not significantly altering the hMSC phenotype by monitoring classic markers of undifferentiated stem cells. RNA was collected just before, and 1, 3, 6, 19, 27, 34, 37, and 41 days after the BIO treatment Results were quantified over time and again, normalized to both the housekeeping gene β-actin and untreated controls (0 μM BIO), and the results are shown in FIG. 5.

Immediately after treatment with BIO (day 1), an increase in stem-cell associated marker expression was observed. Sox2 gene expression was elevated 7.1- and 96.4-fold with 2 μM and 5 μM BIO treatment, compared to the untreated control group (FIG. 5a). Similarly, Nanog gene expression was increased to 5.4- and 15.3-fold (FIG. 5a), and Oct4 gene expression was increased to 5.1- and 16.9-fold untreated control (FIG. 5a).

Stem cell-associated gene expression remained significantly up-regulated in a dose dependent fashion through day 3 before returning to basal levels (FIG. 5b). Sox2, Nanog, and Oct4 gene expression were 4.4- and 17.7-fold, 1.0- and 4.8-fold, and 3.4- and 9.8-fold untreated control for 2 μM and 5 μM BIO treatment respectively. This spike in gene expression coincides with the previously-described enhancement in β-catenin activity (FIG. 3c) indicative of transient BIO-mediated activation of the canonical Wnt/β-catenin signaling pathway.

3.4 Controlled Differentiation of BIO-Treated hMSCs

It is important that these treated hMSC populations maintain their ability to differentiate. To evaluate the ability to differentiate BIO-treated hMSCs, cells were treated with 0 and 5 μM BIO for 24 hrs. The cells were then cultured for an additional 21 days, resulting in similar proliferation as previously described (FIG. 4b) before being differentiated into osteogenic, chondrogenic, and adipogenic lineages as previously described (FIG. 6a).

Histological analysis showed uniform mineralization (osteogenesis, von Kossa), glycosaminoglycan production (chondrogenesis, toludine blue), and lipid droplet accumulation (adipogenesis, oil red o) in comparison between BIO-treated and untreated groups, as illustrated in FIG. 6b. In addition, Cbfa1, Sox9, and PPARγ gene expression was analyzed as markers of osteogenesis, chondrogenesis, and adipogenesis. Interestingly, differentiated BIO-treated hMSCs exhibited a 2.1-fold and 5.0-fold increase in Cbfa1 and PPARγ expression respectively as compared to differentiated non-BIO-treated (0 μM) controls (FIGS. 6c and 6e). Cbfa1 expression for 0 and 5 μM BIO-treated, osteogenic differentiated hMSCs was found to be 1.9- and 3.9-fold over undifferentiated controls (FIG. 6c). PPARγ expression for 0 and 5 μM BIO-treated, adipogenic-differentiated hMSCs was found to be 6.2- and 31.2-fold over undifferentiated controls (FIG. 6e). Although not statistically significant, Sox9 expression for 0 and 5 μM BIO-treated, chondrogenic-differentiated hMSCs was found to be 1.3- and 0.6-fold compared with undifferentiated controls (FIG. 6d).

3.5 Proliferation of BIO-Treated hMSCs Encapsulated in Three-Dimensional PEG Hydrogels BIOs effect on hydrogel-encapsulated hMSCs was evaluated. Cells were encapsulated in PEG hydrogels and treated with BIO-containing media (0 and 5 μM) for 24 hrs (FIG. 7a). Proliferation was assessed by on days 0, 1, 5, 12, and 18 by quantifying hydrogel encapsulated cell DNA concentration. The results shown in FIG. 7b are normalized to initial encapsulated cell DNA concentrations obtained prior to BIO-treatment. Normalized DNA concentration increased, indicating encapsulated hMSC proliferation for both the 0 and 5 μM BIO-treated samples. Moreover, the 5 μM BIO-treated samples exhibited a statistically significant, 20% increase in proliferation at both days 12 and 18. Survivability of hMSCs was verified by LIVE/DEAD staining and confocal imaging (FIG. 7c).

Figure 8:
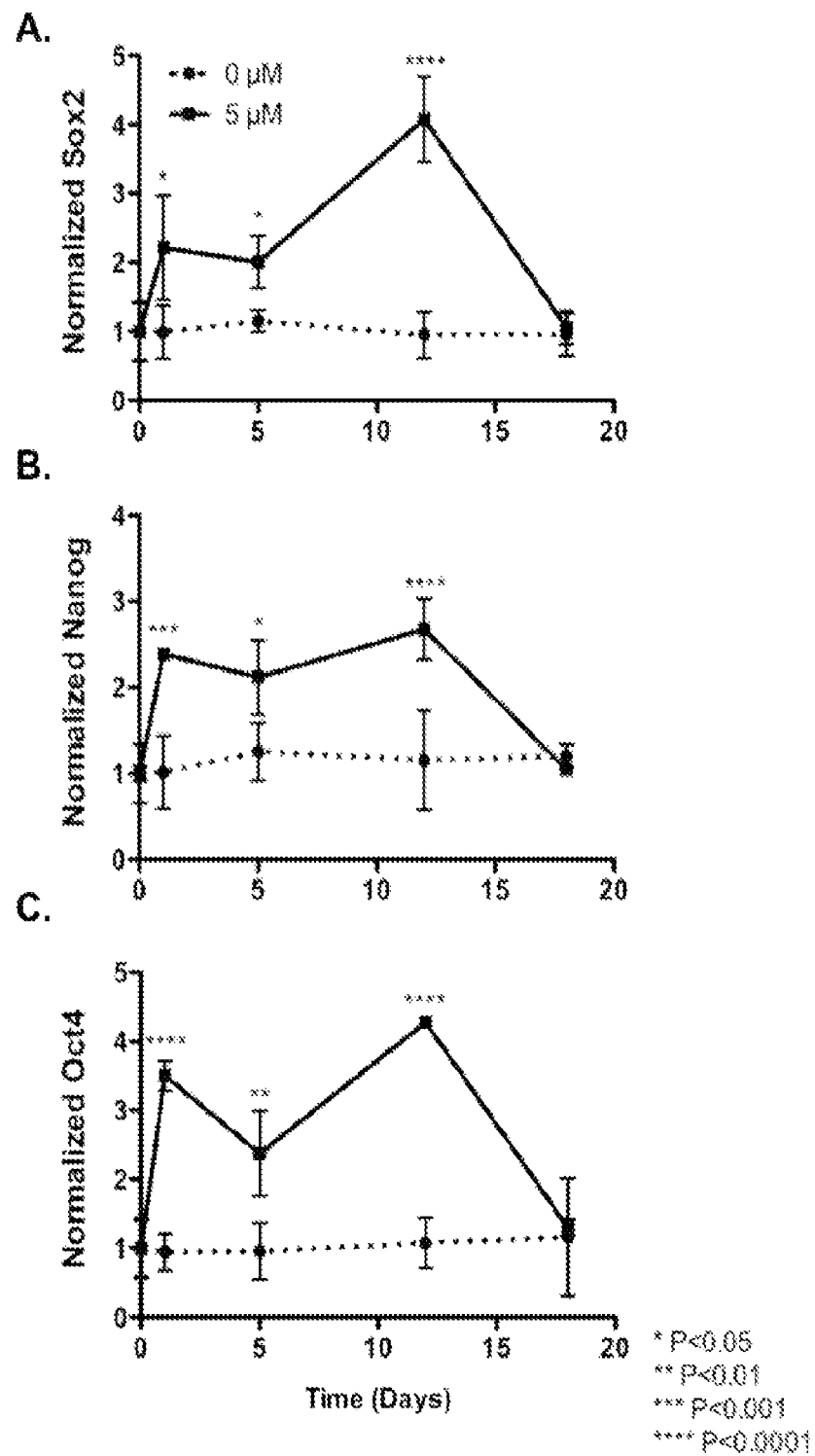
FIG. 8 Gene profiles showing elevated expression of the markers of undifferentiated stem cells, Sox2 (A), Nanog (B), and Oct4 (C) over 18 days following 24 hr exposure of PEG-encapsulated hMSCs to BIO-containing media.

3.6 BIO-Treated hMSC Gene Expression Encapsulated in Three-Dimensional PEG Hydrogels Stem cell associated gene expression profiles for BIO-treated hMSCs encapsulated in PEG hydrogels were analyzed on days 0, 1, 5, 12, and 18 as previously described, and illustrated in FIG. 8. Immediately following BIO-treatment (day 1) Sox2, Nanog, and Oct4 gene expression increased to 2.2-, 2.4, and 3.5-fold untreated controls, respectively. Unlike in the two-dimensional culture conditions, expression of Sox2, Nanog, and Oct4 remained significantly up-regulated through day 12, where expression remained 4.1-, 2.7, and 4.3-fold untreated controls, respectively (FIG. 8a-c). This prolonged enhancement of undifferentiated stem cell marker expression was hypothesized to be a result of prolonged BIO interaction with the PEG-hydrogel microenvironment Expression of Sox2, Nanog, and Oct4 within the PEG hydrogel-encapsulated hMSCs returned to basal levels at ~day 18.

In this work, by shifting the delicate balance of undifferentiated stem cell marker expression and possibly enhancing cell cycle progression we were able to obtain more proliferative MSC population. While Sox2, Nanog, and Oct4 expression were only significantly up-regulated during the initial 3 days of our two-dimensional BIO-treated study it is possible that BIO-mediated MSC Wnt/β-catenin signaling enhances Sox2, Nanog, and Oct4 expression and works to enhance the MSC pluripotent phenotype by inducing a more homogeneous stem cell population.

While the present invention has been shown and described with reference to certain embodiments thereof, it will be understood by those skilled in the art that various changes in form and details may be made therein without departing from the spirit and scope of the invention as described.

REFERENCES

[1] Xie, C., Reynolds, D., Awad, H., et al. Structural bone allograft combined with genetically engineered mesenchymal stem cells as a novel platform for bone tissue engineering. *Tissue Eng.* 13:435. 2007

[2] Zhang, X., Xie, C., Lin, A., et al. Periosteal progenitor cell fate in segmental cortical bone graft transplantations: implications for function tissue engineering. *J Bone Miner Res.* 20:2124. 2005

[3] Polychronopoulos, P., Magiatis, P., Skaltsounis, A., et al. Structural basis for the synthesis of indirubins as potent and selective inhibitors of glycogan synthase kinase-3 and cyclin-dependent kinases. *J. Med. Chem.* 47:935. 2004

[4] Hilton, M. J., Tu, X., Bai, S., et al. Notch signaling maintains bone marrow mesenchymal progenitors by suppressing osteoblast differentiation. *Nat. Med.* 14:306. 2008

[5] Li, J., Khavandgar, Z., Lin, S., et al. Lithium chloride attenuates BMP-2 signaling and inhibits osteogenic differentiation through a novel WNT/GSK3-independent mechanism. *Bone.* 48:321. 2011

[6] Benoit, D. S. W., Nuttelman, C. R., Collins, S. D., et al. Synthesis and characterization of a fluvastatin-releasing hydrogel delivery system to modulate hMSC differentiation and function for bone regeneration. *Biomaterials.* 27:6102. 2006

The invention claimed is:

1. A method for stimulating proliferation of mesenchymal stem cells comprising contacting the cells with a composition comprising 6-bromoindirubin-3'-oxime (BIO) in a concentration sufficient to stimulate proliferation which is greater than proliferation in the absence of BIO, wherein the concentration of BIO is from 2 to 5 μM, and wherein the concentration of 2 to 5 μM of BIO stimulates proliferation of the mesenchymal stem cells.

2. The method of claim 1, wherein the cells are human mesenchymal stem cells.

3. The method of claim 1, wherein the cells are exposed to BIO in vitro.

4. The method of claim 1, wherein the cells are grown on a three dimensional substrate.

5. The method of claim 4, wherein the substrate comprises materials comprising poly(ethylene glycol).

6. The method of claim 3, wherein the cells are contacted with BIO for from 1 to 48 hours and further maintained in vitro for at least 3 days.

7. The method of claim 1, wherein the cells are contacted with BIO in vitro for from 1 to 48 hours and further maintained in vitro for at least 3 days.

8. The method of claim 1, wherein the cells are maintained in culture from 3 to 30 days after removal of BIO.

* * * * *

SEQUENCE LISTING

<160> NUMBER OF SEQ ID NOS: 16

<210> SEQ ID NO 1
<211> LENGTH: 18
<212> TYPE: DNA
<213> ORGANISM: Artificial Sequence
<220> FEATURE:
<223> OTHER INFORMATION: primer

<400> SEQUENCE: 1
aaccagaaaa acagcccg                                                18

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
ttgctgatct ccgagttgtg                                              20

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
gatttgtggg cctgaagaaa                                              20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
cagatccatg gaggaaggaa                                              20

<210> SEQ ID NO 5
<211> LENGTH: 21
<212> TYPE: DNA
<213> ORGANISM: Artificial Sequence
<220> FEATURE:
<223> OTHER INFORMATION: primer

<400> SEQUENCE: 5
gcaagagcac aagaggaaga g                                            21

<210> SEQ ID NO 6
<211> LENGTH: 18
<212> TYPE: DNA
<213> ORGANISM: Artificial Sequence
<220> FEATURE:
<223> OTHER INFORMATION: primer

<400> SEQUENCE: 6
aaggggtcta catggcaa                                                18

<210> SEQ ID NO 7
<211> LENGTH: 22
<212> TYPE: DNA
<213> ORGANISM: Artificial Sequence -continued
<220> FEATURE:
<223> OTHER INFORMATION: primer

<400> SEQUENCE: 7
tgtgatggtg ggaatgggtc ag                                        22

<210> SEQ ID NO 8
<211> LENGTH: 22
<212> TYPE: DNA
<213> ORGANISM: Artificial Sequence
<220> FEATURE:
<223> OTHER INFORMATION: primer

<400> SEQUENCE: 8
tttgatgtca cgcacgattt cc                                        22

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
ctgaagcaga agaggatcac                                           20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
gaccacatcc ttctcgagcc                                           20

<210> SEQ ID NO 11
<211> LENGTH: 22
<212> TYPE: DNA
<213> ORGANISM: Artificial Sequence
<220> FEATURE:
<223> OTHER INFORMATION: primer

<400> SEQUENCE: 11
atgcttcatt cgcctcacaa ac                                        22

<210> SEQ ID NO 12
<211> LENGTH: 24
<212> TYPE: DNA
<213> ORGANISM: Artificial Sequence
<220> FEATURE:
<223> OTHER INFORMATION: primer

<400> SEQUENCE: 12
ccaaaagaag ttttgctgac atgg                                      24

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
tttccaagac acaaacatga                                           20

```
<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
aaagtccagt ttctcgttga                                              20

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
tctctccgta atggaagacc                                              20

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
gcattatgag acatccccac                                              20
```